United States Patent [19]

Freeman

[11] Patent Number: 5,391,187
[45] Date of Patent: Feb. 21, 1995

[54] SEMIAUTOMATIC DEFIBRILLATOR WITH HEART RATE ALARM DRIVEN BY SHOCK ADVISORY ALGORITHM

[75] Inventor: Gary A. Freeman, Newton Centre, Mass.

[73] Assignee: ZMD Corporation, Wilmington, Del.

[21] Appl. No.: 200,781

[22] Filed: Feb. 22, 1994

[51] Int. Cl.$^6$ ............................................. A61N 1/39
[52] U.S. Cl. ........................................ 607/5; 607/4; 128/706
[58] Field of Search ....................... 607/2, 4, 5, 7, 119; 128/696, 697, 702, 703, 706

[56] References Cited

U.S. PATENT DOCUMENTS

| | | | |
|---|---|---|---|
| 3,614,955 | 10/1971 | Mirowski et al. | 128/419 D |
| 3,716,059 | 2/1973 | Welborn et al. | 128/419 D |
| 3,757,791 | 9/1973 | Berkovits | 128/419 |
| 4,088,138 | 5/1978 | Diack et al. | 128/419 |
| 4,184,493 | 1/1980 | Langer et al. | 128/419 |
| 4,202,340 | 5/1980 | Langer et al. | 128/419 |
| 4,223,678 | 9/1980 | Langer et al. | 128/419 |
| 4,296,755 | 10/1981 | Judell | 128/705 |
| 4,360,030 | 11/1982 | Citron et al. | 128/702 |
| 4,453,551 | 6/1984 | Anderson et al. | 128/704 |
| 4,475,551 | 10/1984 | Langer et al. | 128/419 |
| 4,523,595 | 6/1985 | Zibell | 128/419 |
| 4,574,810 | 3/1986 | Lerman | 128/419 |
| 4,583,553 | 4/1986 | Shah et al. | 128/704 |
| 4,619,265 | 10/1986 | Morgan et al. | 128/419 |
| 4,635,639 | 1/1987 | Hakala et al. | 128/419 |
| 4,769,620 | 1/1989 | Imran | 128/706 |
| 4,919,144 | 4/1990 | Vandehey | 128/705 |
| 4,960,123 | 10/1990 | Maker | 128/419 |
| 5,184,620 | 2/1993 | Cudahy et al. | 607/4 |
| 5,284,135 | 2/1994 | Lopin | 607/4 |

FOREIGN PATENT DOCUMENTS 2083363A 3/1982 United Kingdom .

OTHER PUBLICATIONS

Stratbucker et al., "Automatic Cardioversion Using Electronics Arhythmia Logic".

Thurer et al., "Automatic Implantable Cardioverter-Defibrillator: Techniques of Implantation and Results", The annals of Toracic Surgery, vol. 42, No. 2, pp. 143-147, Aug. 1986.

Mower et al., "Automatic Implantable Cardioverter-Defibrillator Structural Characteristics", PACE, vol. 7, pp. 1332-1337, Nov.-Dec. 1984, Part II.

Mirowski et al., "The Automatic Implantable Defibrillator", PACE, vol. 5, pp. 384-401, May-Jun. 1982.

*Primary Examiner*—George Manuel
*Attorney, Agent, or Firm*—Fish & Richardson

[57] ABSTRACT

A defibrillator with an alarm driven by both a heart rate detector and a fibrillation/tachycardia advisory algorithm. The defibrillator is a semiautomatic. By driving the alarm from both sources, the operator is provided with more information; instead of simply being advised of the onset of fibrillation or shockable tachycardia, the operator of a semiautomatic defibrillator is now also advised of the onset of asystole, bradycardia, and non-shockable tachycardia (e.g., superventricular tachycardia). The advisory algorithm can often provide a more timely indication of the onset of an abnormal rhythm than can the conventional heart rate detector, which relies on averaging over multiple heart beats, and thus is slow to detect a change in waveform. And, the advisory algorithm will sometimes detect an abnormal ECG that would have gone undetected by a conventional heart rate alarm. The defibrillator can be combined with an external pacemaker, so that both defibrillation and pacing are available to respond to the conditions detected by the improved alarm. For example, if asystole or bradycardia is detected, the unit can provide pacing stimuli rather than defibrillation stimuli.

6 Claims, 5 Drawing Sheets

OTHER PUBLICATIONS

Arzbaecher et al., "Automatic Tachycardia Recognition", PACE, vol. 7, pp. 541–547, May–Jun. 1984, Part II.

Mirowski et al., "A Chronically Implanted System for Automatic Defibrillation in Active Conscious Dogs" Circulation, vol. 58, No. 1, pp. 90–94, Jul. 1978.

Jenkins et al., "Computer Diagnosis of Supraventricular and Ventricular Arrhythmias", Circulation, vol. 60, No. 5, pp. 977–985, Nov. 1979.

Langer et al., "Considerations in the development of the automatic implantable defibrillator", Medical Instrumentation, vol. 10, No. 3, May–Jun. 1976.

Winkle, "The Implatable Defibrillator in Ventricular Arrhythmias", Hospital Practice, pp. 149–156, 161–165, Mar. 1983.

Cannom et al., "Implantation of the Automatic Implantable Cardioverter Defibrillator (ACID): Practical Aspects", PACE, vol. 9, pp. 793–809, Nov.–Dec. 1986, Part I.

Mirowski et al., "Standby Automatic Defibrillator", Arch Intern Med, vol. 126, pp. 158–161, Jul. 1970.

Jenkins et al., "Tachycardia Detection in Implantable Antitachycardia Devices", PACE, vol. 7, pp. 1273–1277, Nov.–Dec. 1984, Part II.

SEMIAUTOMATIC DEFIBRILLATOR WITH HEART RATE ALARM DRIVEN BY SHOCK ADVISORY ALGORITHM

BACKGROUND OF THE INVENTION

This invention relates to semiautomatic defibrillators, in which an advisory algorithm advises an operator as to whether a shock should be delivered, and it is left to the operator to initiate delivery of the shock.

Semiautomatic defibrillators are well known. They have been in use in one form or another for nearly twenty years. An advisory algorithm analyzes a patient's electrocardiogram (ECG), and gives the operator an advisory indication of whether a shock should be delivered. Typically, the advisory algorithm analyzes the ECG for both ventricular fibrillation and shockable high rate tachycardia. If either is found, the unit will advise the operator that a shock should be delivered. The operator then simply presses a button to deliver the shock. Such units typically have a standby mode used after a patient has been stabilized (e.g., while the patient is being transported to a hospital), in which an alarm will sound indicating that the patient should be checked. The same advisory algorithm, which checks for ventricular fibrillation and shockable tachycardia, is used to trigger the alarm. Following such an alarm, the operator is expected to initiate a further analysis of the ECG, and then to deliver a shock if the advisory algorithm so recommends.

In manual defibrillators, the type of units used by physicians and nurses, and by highly-skilled EMTs, the automated ECG analysis found in semiautomatic units is not provided, and instead the operator is required to makes his or her own decision whether to apply a shock based on a display of the ECG. But it is typical to provide the operator with a heart rate alarm, which is triggered when the QRS detector (essentially a heart rate tachometer) indicates that the heart rate is above or below preset limits. Ordinarily, the heart rate is averaged over several heart beats in order to improve its accuracy. The alarm is useful for signalling an operator of asystole (no heart activity), bradycardia (abnormally slow heart rate), or tachycardia (abnormally high heart rate).

Monitoring equipment of the type used in the cardiac care units (CCUs) of a hospital perform a variety of tests on the ECG, including both heart rate as well as analysis for fibrillation and tachycardia, but these units are for monitoring only, and provide no defibrillation stimuli.

External pacing units have provided heart rate alarms of the same sort as found in manual defibrillators. Such units are typically used by the same skilled practitioners as operate manual defibrillators.

SUMMARY OF THE INVENTION

In general the invention features a defibrillator with an alarm driven by both a heart rate detector and a fibrillation/tachycardia advisory algorithm. Preferably the defibrillator is a semiautomatic. By driving the alarm from both sources, the operator is provided with more information than has heretofore been available. For example, instead of simply being advised of the onset of fibrillation or shockable tachycardia, the operator of a semiautomatic defibrillator is now also advised of the onset of asystole, bradycardia, and nonshockable tachycardia (e.g., superventricular tachycardia). But there are surprising further benefits. The advisory algorithm, it turns out, can often provide a more timely indication of the onset of an abnormal rhythm than can the conventional heart rate detector, which relies on averaging over multiple heart beats, and thus is slow to detect a change in waveform. And, the advisory algorithm will sometimes detect an abnormal ECG that would have gone undetected by a conventional heart rate alarm.

In preferred embodiments, the semiautomatic defibrillator is combined with an external pacemaker, so that both defibrillation and pacing are available to respond to the conditions detected by the improved alarm. For example, if asystole or bradycardia is detected, the unit can provide pacing stimuli rather than defibrillation stimuli.

Other features and advantages of the invention will be apparent from the following description of preferred embodiments, and from the claims.

Figure 1:
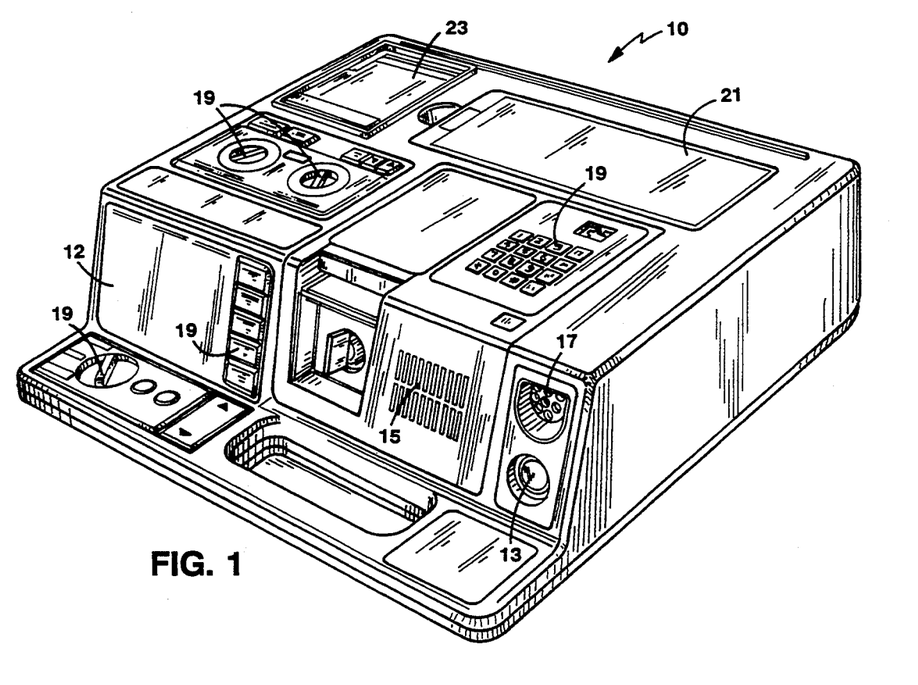
FIG. 1 is a perspective view of a semiautomatic defibrillator embodying the invention.

Shown in FIG. 1 is a semiautomatic defibrillator 10. The defibrillator monitors the electrocardiograph (ECG) signal of a patient (received from ECG electrodes 14), displays the ECG signal (and other information) on a video monitor 12, analyzes the ECG signal to detect shockable waveforms, provides an advisory indication on the monitor (and with voice prompts from speaker 15) when a shockable waveform is detected and a shock is advised, and provides a shock discharge switch 13 by which the user may administer a shock if a shockable waveform has been detected. The shock is delivered through disposable electrodes adhesively applied to the patient's chest. The electrodes are coupled to the defibrillator at connecter 17. Optionally, the defibrillator also includes cardiac pacing capability, and both pacing and defibrillation stimuli are delivered through multi-function electrodes 17, which are adhesively adhered to the chest wall. Various control knobs and buttons 19 are provided, some of which are only operable in a manual mode which is only made available to qualified operators. A battery is stored in compartment 21. Strip chart recording can optionally be provided by recorder 23.

Figure 2:
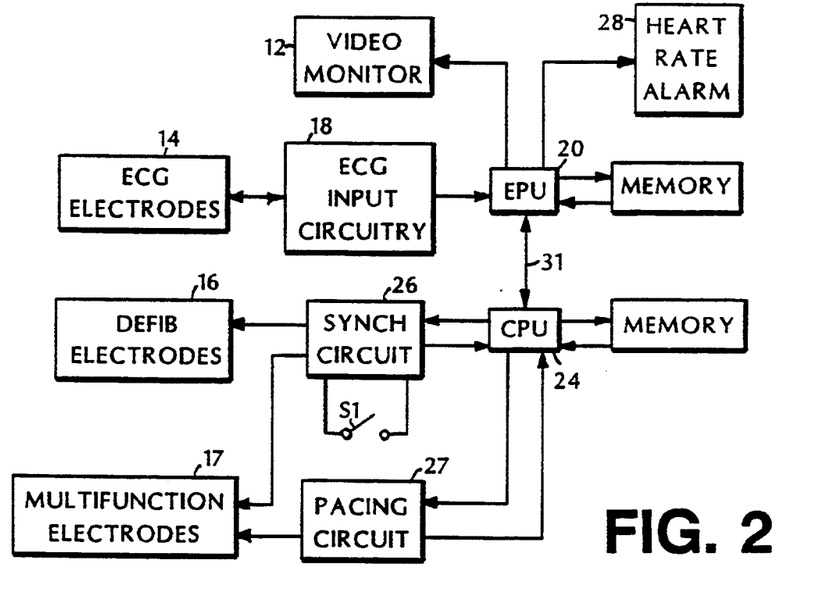
FIG. 2 is a block diagram of the electrical aspects of the defibrillator of FIG. 1.

Turning to the block diagram of FIG. 2, the output of ECG electrodes 14 is received by input circuitry 18 (e.g., input filters and analog-to-digital converters) and fed to ECG processor (EPU) 20. The ECG processor runs the advisory algorithm that processes the ECG signal to detect shockable waveforms, and controls the monitor on which the ECG signal and advisory indications are displayed. The ECG processor communicates with central processor (CPU) 24 via a bidirectional serial interface 31. The ECG processor determines whether a waveform is shockable, and if so at what point in time the shock should be delivered. The shock synchronization point is communicated to the CPU via a hardware interrupt line separate from the normal serial communication interface bus. A handwired interrupt is used in order to minimize the latency time between the actual cardiac event and the defibrillation shock. A number of factors affect latency time, including delays due to handwired (analog) filters, software (digital) filters, software waveform analysis algorithms, inter- and intraprocessor communication latencies, interrupt latency, and high-voltage relay actuation time. The latency time should be kept below approximately 60 mS for maximum beneficial effect. The central processor communicates with a shock synchronizing circuit 26, which includes operator-controlled discharge switch S1. A heart rate alarm (both visual and auditory) 28 is also controlled by the ECG processor. If pacing is included in the defibrillator, the central processor also controls a pacing circuit 27, and the pacing stimulus may either be delivered through separate pacing electrodes (not shown) or multi-function electrodes, to which both the defibrillation and pacing outputs are connected.

The shock advisory algorithm 30 (FIG. 5) implemented by the ECG processor may be of conventional design. The outputs of the algorithm (indicating whether a shock or no-shock decision has been reached) are supplied to the central processor (CPU). The algorithm must be able to distinguish between shockable waveforms (e.g., high-rate tachycardia and ventricular fibrillation) and nonshockable waveforms. And it must also be able to distinguish between high rate tachycardia (VTACH) and ventricular fibrillation (VF), as shock synchronization is performed differently for the two conditions. Algorithms and techniques therefor are taught in U.S. Patent Nos. 4,919,144; 4,796,620; 4,635,639; 4,619,265; 4,583,553; 4,523,595; 4,453,551; 4,295,474; 4,275,742; 4,202,340; 4,088,138; 3,807,392; 3,805,795; 3,616,790; 3,612,041; and 3,554,187; and in the following publications: W. A. Tacker, Defibrillation of the Heart, 1994 Mosby Yearbook; D. Craig Edwards, "Development of a Decision Algorithm for a Semi-Automatic Defibrillator," *Annals of Emergency Medicine*, 18:12, December 1989, 1276–1279; C. M. Jack, "An External Automatic Device to Detect Ventricular Fibrillation," *European Heart Journal*, 7, 1986, 404–411; S. Kuo, "Computer Detection of Ventricular Fibrillation," Computers in Cardiology, September 1978, 347–349; F. K. Forster, "Recognition of Ventricular Fibrillation, Other Rhythms and Noise in Patients Developing the Sudden Cardiac Death Syndrome"; and H. Ozemek, "Detection of Ventricular Fib. by Microcomputer," Journal of Clinical Engineering, Vol. 6, No. 3, 1981, p. 203–207.

The ECG processor also implements a QRS detector 32 (FIG. 5) and a QRS width and morphology detector 34, both as known in the prior art, for example, as taught in U.S. Patent Nos. 4,667,682; 4,184,487; 4,083,366; 4,034,745; 4,022,192; 3,978,856; 3,858,574; 3,773,038; 3,650,263; 3,648,689; 3,513,833; and in the following publications: A. Cohen, Biomedical Signal Processing CRC Press, 1986; W. Thompkins, "A Real Time QRS Detection Algorithm," IEEE Transactions on Biomedical Eng., Vol. BM-C32, No. 3, March 1985, 230–236; C. Mead, "Development and Evaluation of a New QRS Detector/Delineator," Computers in Cardiology, September 1979, 251–254; P. E. Trahanias, "Syntactic Pattern Recognition of the ECG," IEEE Trans. Pattern Anal Mach. Intell., Vol. PAMI-12, pp. 648–657, July 1990; and M. E. Nygards, "Delineation of the QRS Complex Using the Envelope of the ECG," Med. & Biol. Eng. & Computing, September 1983, 538–547.

Figure 5:
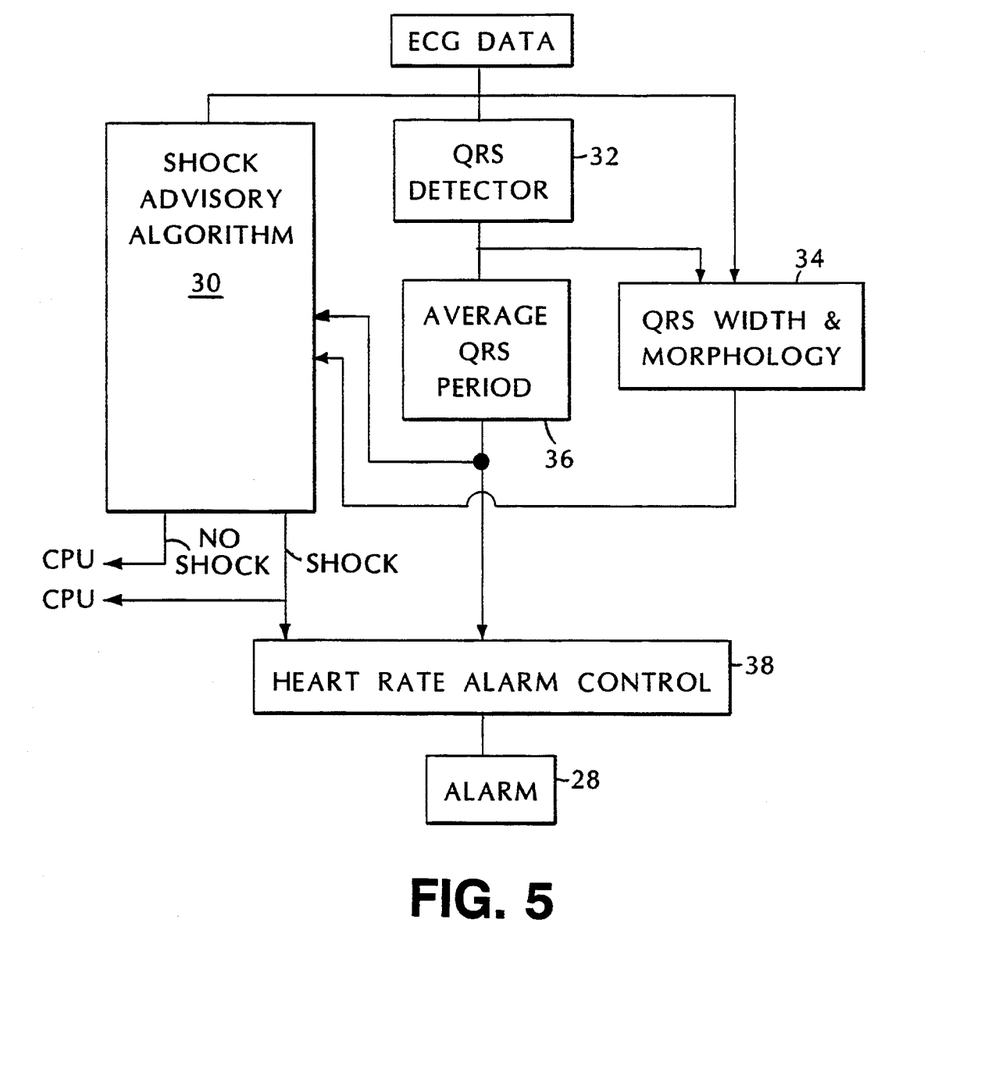
FIG. 5 is a flow chart of the steps followed by the defibrillator of FIG. 1 in activating a heart rate alarm.

The average period between QRS wave complexes is calculated (36) by averaging the period of time between R-waves. Average QRS period and QRS width and morphology information are passed to the shock advisory algorithm 30 and to the heart rate alarm control 38, which activates alarm 28.

In addition to supplying the heart rate alarm control with QRS period, the alarm control logic is also supplied with an output of the shock advisory algorithm indicating whether a shockable waveform has been detected. The control logic activates the heart rate alarm when the algorithm has detected a shockable waveform or the average QRS period exceeds a threshold. The alarm is provided visually on monitor 12 and audibly by speaker 15 (e.g., by a "CHECK PATIENT" warning). The alarm logic can also optionally control whether the stimulus delivered is a defibrillation shock or a pacing stimulus; e.g., if asystole or bradycardia (zero or low heart rate) is detected, the stimulus delivered could be a pacing stimulus. For instance, it is not uncommon for the patient suffering from cardiac arrest to be converted with defibrillation to a bradycardiac rhythm which is properly treated with pacing. Thus, after defibrillation, if bradycardia is detected, the patient could be automatically treated with pacing stimuli.

If the output of the shock advisory algorithm advises delivery of a shock, a message to that effect is displayed on monitor 12. The operator may then administer the shock by closing switch S1. But unlike the operation in conventional semiautomatic defibrillators, the shock is not immediately administered when the operator activates switch S1. Instead, the defibrillator delays administration of the shock in an effort to synchronize its delivery with a desired ECG event. If the advisory algorithm has detected high-rate tachycardia, then the triggering ECG event is the occurrence of an R-wave. On the other hand, if the advisory algorithm has detected ventricular fibrillation, the triggering ECG event is a high peak in the ECG (e.g., an absolute ECG signal level greater than a predetermined percentage of the average absolute magnitude of the ECG).

Figure 3:
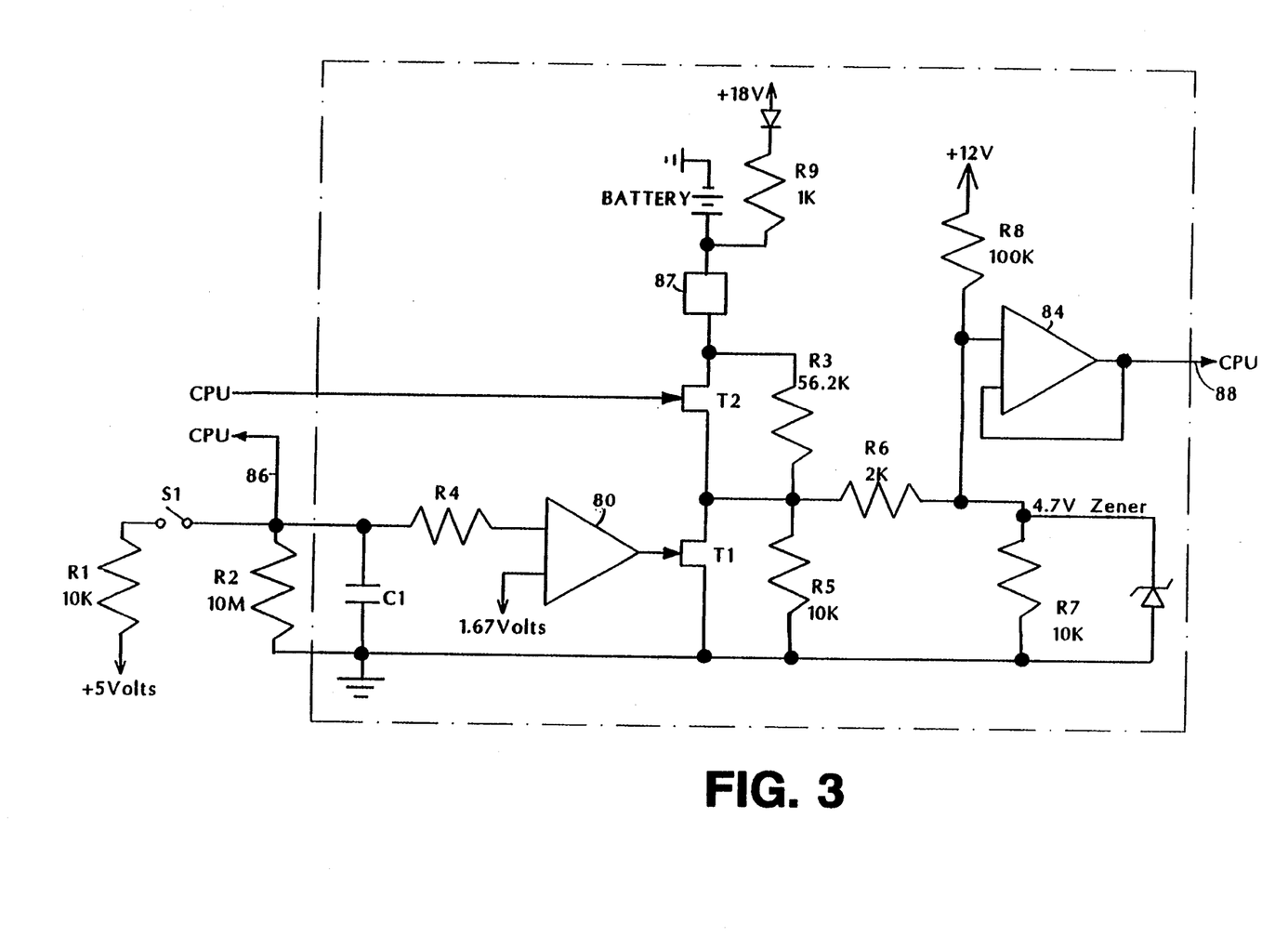
FIG. 3 is a circuit diagram of the shock timing circuit of FIG. 2.
Figure 4:
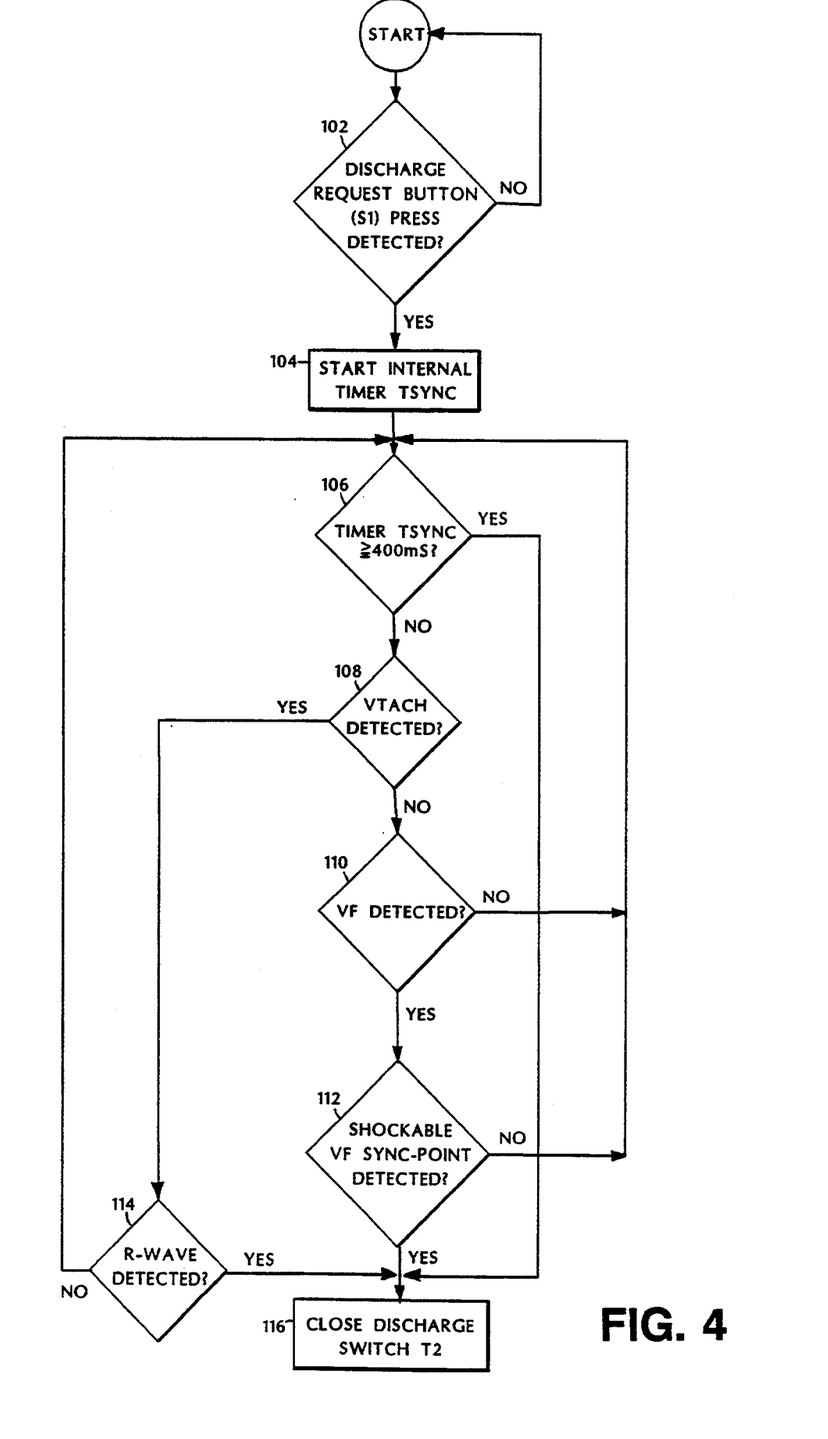
FIG. 4 is a flow chart of the steps followed by the defibrillator of FIG. 1 in delivering a shock.

Synchronization is accomplished using the synchronizing circuit of FIG. 3 and the processor-implemented steps of FIG. 4. When the processor detects (102, FIG. 4) that the user has closed discharge request switch S1 (FIG. 3), a software-implemented 400 msec timer TSYNCH is started (104). Closure of switch S1 also has the effect of closing FET switch T1 for a period of about 500 msec (the period set by the delay circuit comprised of C1, R2 and the comparator 80). During the next 400 msec period, the processor determines whether the advisory algorithm has detected high rate tachycardia (VTACH) (108) or ventricular fibrillation (VF) (110). If high rate tachycardia has been detected by the algorithm, then the processor waits for detection of a R-wave (114). If an R-wave is detected, the processor initiates delivery of a shock to the patient, by activating discharge FET switch T1, which, in turn, activates patient relay coil 82 (FIG. 3). If ventricular fibrillation has been detected, the processor waits for detection of VF synch-point in the ECG signal (e.g., an absolute ECG signal level greater than a predetermined percentage of the average absolute magnitude of the ECG). If the synch-point is detected, the processor delivers a shock to the patient (by activating switch T1). If the 400 msec period expires (106, FIG. 4) without a triggering ECG event being detected, the processor still initiates delivery of a shock.

The processor is able to check the integrity of FET switches T1, T2, and other aspects of the circuit of FIG. 3, by sampling the voltages at two points (86, 88). The circuit provided by resistors R3, R5–R9 and amplifier 84 aid in this diagnosis.

Other embodiments are within the scope of the following claims. For example, the maximum delay period between closure of switch S1 and administration of the shock may be varied (preferably within a range of 50 msec to 5 sec).

What is claimed is:

1. A semiautomatic cardiac defibrillator for receiving an ECG signal from a patient, providing an advisory indication to an operator, and allowing the operator to initiate delivery of a defibrillating shock to a patient through electrodes applied to the patient's chest, said defibrillator comprising:

an input circuit for receiving an ECG signal from the patient;

processing circuitry connected to the input circuit for processing the ECG signal to determine an average QRS rate and to determine whether to issue a shock advisory indication recommending delivery of a shock;

a display for displaying the advisory indication to the operator;

energy storage circuitry for generating a defibrillating shock for delivery to the patient;

an output circuit for delivering the defibrillating shock to the electrodes;

a manually operable switch controlling the output circuit, the switch being capable of being moved by the operator to a position in which a shock is delivered to the electrodes if there is an advisory indication recommending delivery of a shock; and a heart rate alarm circuit in which the inputs comprise an averaged QRS rate and the shock advisory indication.

2. The semiautomatic cardiac defibrillator of claim 1 further comprising a pacing circuit for delivering a pacing stimulus to electrodes capable of delivering the stimulus.

3. The semiautomatic cardiac defibrillator of claim 2 wherein the heart rate alarm circuit activates the pacing circuit when the alarm circuit detects the presence of asystole or bradycardia.

4. A method of semiautomatic cardiac defibrillation in which an ECG signal is received from a patient, an advisory indication is provided to an operator, and the operator is allowed to initiate delivery of a defibrillating shock to a patient through electrodes applied to the patient's chest, the method comprising the steps of:

receiving an ECG signal from the patient;

processing the ECG signal to determine an average QRS rate and to determine whether to issue a shock advisory indication recommending delivery of a shock;

displaying the advisory indication to the operator;

generating a defibrillating shock for delivery to the patient;

delivering the defibrillating shock to the electrodes;

providing a manually operable switch controlling the output circuit, the switch being capable of being moved by the operator to a position in which a shock is delivered to the electrodes if there is an advisory indication recommending delivery of a shock; and providing a heart rate alarm circuit for which the inputs comprise an averaged QRS rate and the shock advisory indication.

5. The method of claim 4 further comprising the step of delivering a pacing stimulus to the patient.

6. The method of claim 5 wherein the heart rate alarm circuit activates the pacing circuit when the alarm circuit detects the presence of asystole or bradycardia.

* * * * *

UNITED STATES PATENT AND TRADEMARK OFFICE
CERTIFICATE OF CORRECTION

PATENT NO. : 5,391,187

DATED : February 21, 1995

INVENTOR(S) : Gary A. Freeman

It is certified that error appears in the above-identified patent and that said Letters Patent is hereby corrected as shown below:

Cover page, under [56] References Cited, U.S. PATENT DOCUMENTS, "4,769,620" should be --4,796,620--.

Cover page, under [56] References Cited, OTHER PUBLICATIONS, within the "Stratbucker et al." reference, "Electronics Arhythmia" should be --Electronic Arrhythmia--.

Signed and Sealed this

Ninth Day of May, 1995

Attest:

BRUCE LEHMAN

Attesting Officer

Commissioner of Patents and Trademarks